(12) United States Patent  
Morrison (10) Patent No.: US 12,013,267 B2  
(45) Date of Patent: Jun. 18, 2024

(54) SYSTEM AND METHOD FOR MEASURING FLUID FLOW FROM A SYRINGE

(71) Applicant: WEST PHARMACEUTICAL SERVICES, INC., Exton, PA (US)

(72) Inventor: Mark Steven Morrison, Basking Ridge, NJ (US)

(73) Assignee: West Pharmaceutical Services, Inc., Exton, PA (US)

( * ) Notice: Subject to any disclaimer, the term of this patent is extended or adjusted under 35 U.S.C. 154(b) by 349 days.

(21) Appl. No.: 17/622,195

(22) PCT Filed: Jun. 30, 2020

(86) PCT No.: PCT/US2020/040315  
§ 371 (c)(1),  
(2) Date: Dec. 22, 2021

(87) PCT Pub. No.: WO2021/003164  
PCT Pub. Date: Jan. 7, 2021

(65) Prior Publication Data  
US 2022/0412783 A1     Dec. 29, 2022

Related U.S. Application Data

(60) Provisional application No. 62/869,139, filed on Jul. 1, 2019.

(51) Int. Cl.  
    *G01F 1/36*     (2006.01)  
    *A61M 5/31*     (2006.01)  
    (Continued)

(52) U.S. Cl.  
    CPC .............. *G01F 1/36* (2013.01); *A61M 5/3129* (2013.01); *A61M 5/3135* (2013.01);  
(Continued)

(58) Field of Classification Search  
CPC ...... G01F 1/36; A61M 5/3129; A61M 5/3135  
See application file for complete search history.

(56) References Cited

U.S. PATENT DOCUMENTS 10,046,144 B2 * 8/2018 Lampropoulos ............................ A61M 25/10182  
10,653,831 B2 * 5/2020 Willoughby ...... A61M 5/31515  
(Continued)

FOREIGN PATENT DOCUMENTS

| WO | WO-0044431 A1 * | 8/2000 | ...... A61M 25/10182 |
| WO | 2018/083062 A1 | 5/2018 | |
| WO | 2019/122027 A1 | 6/2019 | |

OTHER PUBLICATIONS

WO-0044431-A1 English (Year: 2000).*

*Primary Examiner* — Ryan D Walsh  
(74) *Attorney, Agent, or Firm* — Blank Rome LLP (57) ABSTRACT

A device and method for measuring a volume of liquid expelled from a syringe is provided. The device generally includes a syringe barrel, a plunger actuated with a plunger rod, and a sensor. The sensor may include two ports with one port being in fluid communication with a source of fluid external to the syringe barrel, while the second port is in fluid communication either with a proximal end portion of the syringe barrel or a hollow plunger rod having a first end closed by the plunger. The method may include expelling liquid from the syringe; detecting and recording differential pressure with the sensor over time; and calculating the volume of liquid expelled from the syringe from the recorded differential pressure over time.

20 Claims, 8 Drawing Sheets

(51) Int. Cl.
*A61M 5/315* (2006.01)
*A61M 5/48* (2006.01)

(52) U.S. Cl.
CPC .... *A61M 5/31513* (2013.01); *A61M 5/31533* (2013.01); *A61M 5/31568* (2013.01); *A61M 5/486* (2013.01); *A61M 2205/3331* (2013.01); *A61M 2205/3334* (2013.01); *A61M 2205/50* (2013.01)

(56) References Cited

U.S. PATENT DOCUMENTS

2007/0264130 A1    11/2007  Mallett
2011/0224610 A1*  9/2011  Lum ................... A61M 5/3145
                                                141/2
2014/0288408 A1*  9/2014  Deutsch ............. A61M 16/044
                                              128/207.14

\* cited by examiner

SYSTEM AND METHOD FOR MEASURING FLUID FLOW FROM A SYRINGE

CROSS-REFERENCE TO RELATED APPLICATION

This application is a National Stage of International Patent Application No. PCT/US2020/040315, filed on Jun. 30, 2020, which claims the benefit of and priority to U.S. Provisional Application Ser. No. 62/869,139, filed on Jul. 1, 2019, the contents of which are incorporated by reference herein in their entirety.

BACKGROUND

A system and method for measuring the fluid flow from a syringe is provided, which in one embodiment, includes a device comprising a syringe and a sensor configured to measure pressure-differential cause by a flow of fluid on the non-drug contact side of the syringe plunger. Another embodiment relates to a method of measuring the fluid flow from a syringe using a device as disclosed herein.

Medicines and therapeutic agents are often administered not by a health professional, but by the patient requiring treatment. For example, treatment for diabetic patients often requires the regular self-injection of insulin. Therefore, patient adherence to a regiment of accurately dosed therapeutic agents is critical to the long-term health of many patients. Unfortunately, there is a lack of devices that can measure and monitor patient adherence to a regiment of injectable therapies that will provide a physician or other healthcare professional the opportunity to confirm the accuracy and consistency of the patient's injections. Some devices, such as wearable injection devices, injection pens, autoinjectors and infusion pumps, have been developed for some specific therapeutic agents; however, the devices are generally complex and incompatible with a standard pre-fillable syringe.

Therefore, there is a need for improved systems and methods of monitoring patent adherence to a regiment of injectable therapeutic agents capable of monitoring both usage and the dose delivered.

BRIEF SUMMARY OF THE DISCLOSURE

In one aspect, a device is provided that comprises a syringe barrel, a plunger, and a sensor. The syringe barrel may include an internal volume including a proximal end portion and a distal end portion. The plunger may be located within the syringe barrel and configured to slide within the syringe barrel from the proximal end portion towards the distal end portion and provide a seal between the proximal end portion and the distal end portion. The sensor may include a first and second port, the first port being in fluid communication with the proximal end portion and the second port being in fluid communication with a source of fluid external to the proximal end portion of the syringe barrel.

In another aspect, a device is provided that comprises a syringe barrel, a plunger, a sensor, and a hollow plunger rod. The syringe barrel may include an internal volume including a proximal end portion and a distal end portion. The plunger may be located within the syringe barrel and configured to slide within the syringe barrel from the proximal end portion towards the distal end portion and provide a seal between the proximal end portion and the distal end portion. The sensor may include a first and second port, the second port being in fluid communication with a source of fluid external to the syringe barrel. The hollow plunger rod may include a first end closed by the plunger and second end in fluid communication with the first port.

According to yet another aspect, a method of measuring a volume of liquid expelled from a device is provided. The device may be one of the embodiments as previously described, but further comprising a liquid orifice in the distal end portion of the syringe barrel, and the distal end portion of the internal volume of the syringe barrel is filled with a liquid. The method comprises sliding the plunger from the proximal end portion towards the distal end portion to expel liquid through the liquid orifice; detecting and recording differential pressure with the sensor over time; and calculating the volume of liquid expelled through the orifice from the recorded differential pressure over time.

These and other aspects of the various embodiments disclosed herein will be apparent in view of the following description.

BRIEF DESCRIPTION OF THE SEVERAL VIEWS OF THE DRAWINGS

Various aspects and embodiments of the application will be described with reference to the following figures. It should be appreciated that the figures are not necessarily drawn to scale. The figures depict one or more implementations in accord with the present concepts, by way of example only, not by way of limitations. In the figures, like reference numerals may refer to the same or similar elements.

DETAILED DESCRIPTION

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the liquid transfer device, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

It will also be appreciated by those skilled in the art that modifications may be made to the exemplary embodiments described herein without departing from the invention. Structural features of systems and apparatuses described herein may be replaced with functionally equivalent parts. Moreover, it will be appreciated that features from the embodiments may be combined with each other without departing from the disclosure.

Generally, the devices according to the various embodiments disclosed herein provide a means of monitoring drug adherence for an injectable device while also providing a reasonable estimate of the actual drug released by such devices. Unlike other approaches, which focus on the motion of a syringe plunger (or plunger rod) with respect to a fixed point on the syringe barrel, the devices according to various embodiments disclosed herein use a sensor, such as a pressure sensor, to detect the flow of fluid, preferably ambient air, that enters the open end of a syringe barrel (i.e, the non-drug contact side of the plunger) while the drug is being released out of the opposing end of the syringe. Such flow can be integrated to give a reasonable estimate of drug volume dispensed by the syringe because the flow depends on proper function, not just movement, of the plunger.

The devices according to the various embodiments disclosed herein provide an objective means of monitoring patient adherence to injected drug usage, not only that the drug was taken, but also how much of the dose was actually delivered by monitoring the air entering the proximal end portion of the syringe barrel as drug is expelled from the opposite distal end portion of the syringe barrel. The various embodiments disclosed herein may be suitable for use in combination with a pre-filled syringe, pen injector, or an autoinjector, for example. Specifically, the devices disclosed herein may provide a level of resolution that is well-suited for low volume syringes, such as 1 mL (or less) pre-filled syringes. In another example, one potential application for the devices disclosed herein may be a device that delivers insulin.

In yet another example, the devices disclosed herein may be incorporated into a pen injector or infusion pump to provide a means for estimating the delivery drug volume without an electronic or mechanical connection with the injector mechanism used to dispense the medicine. Instead, the device disclosed herein may simply comprise a sensor in fluid communication with the syringe and an enclosure or housing containing the syringe to be well-sealed. The sensor may be placed anywhere within the housing that is convenient, making it possible to retrofit existing injection systems without major modification. Having the ability to locate the sensor remotely from the syringe may provide a desirable solution that avoids intimate interaction with the syringe.

Figure 1:
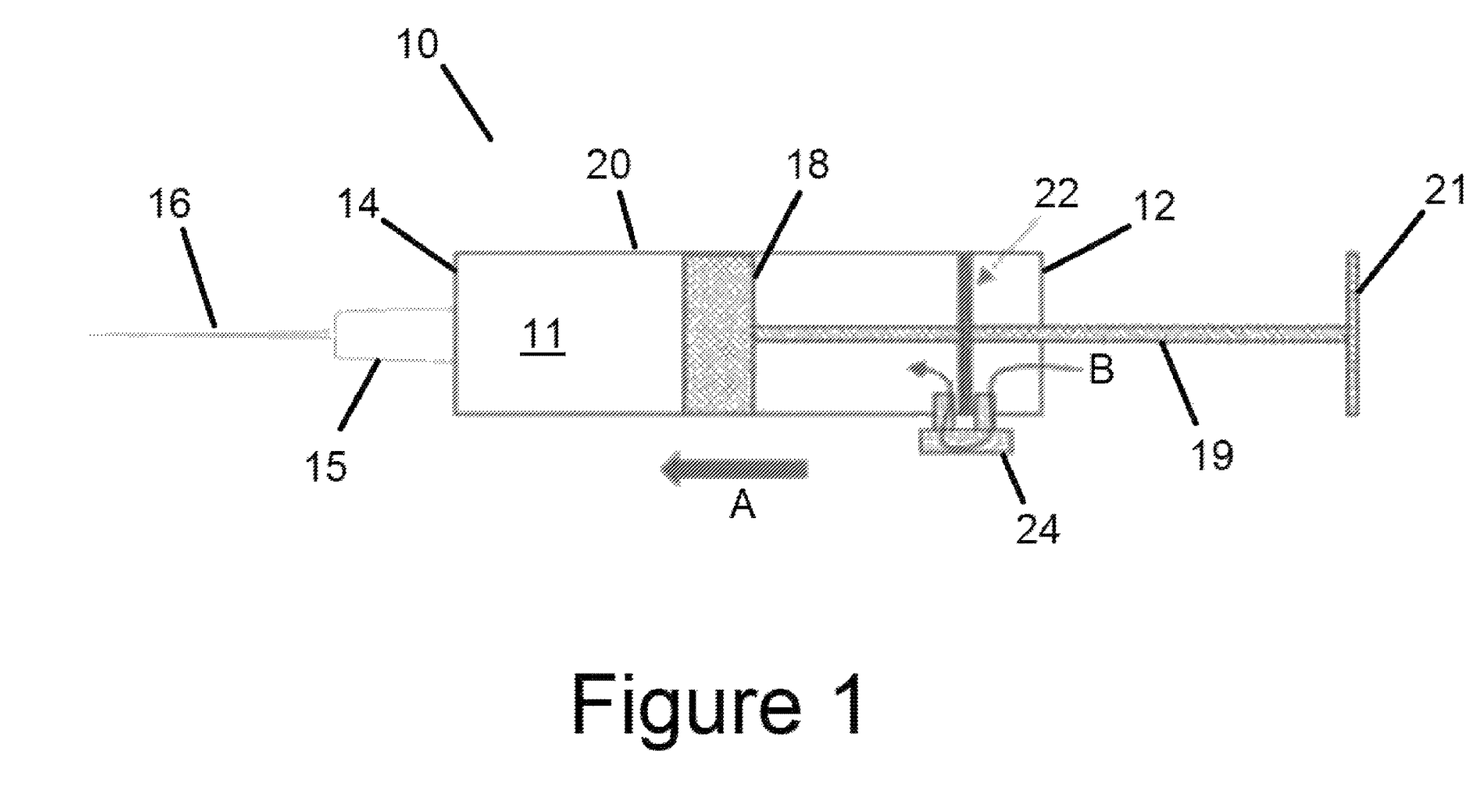
FIG. 1 is a schematic side view of a device according to a first embodiment.

Referring now to FIG. 1, a device according to a first embodiment is provided comprising a syringe 10 having a proximal end portion 12 and a distal end portion 14. The proximal end portion 12 is located on the opposing end of the syringe 10 relative to the distal end portion 14. The distal end portion 14 of the syringe 10 may include a hub 15 having an orifice through which liquid medicine 11 contained in the distal end portion 14 may be expelled. The hub 15 may optionally contain a needle or cannula 16 within or in fluid communication with the orifice.

The syringe 10 comprises a syringe barrel 20 having an internal volume that is separated by a plunger 18. The plunger 18 is inserted into the barrel 20 of the syringe 10 and is configured to slide from the distal end portion 14 towards the proximal end portion 12 of the syringe (as indicated by arrow A). In order to actuate the plunger 18, a plunger rod 19 may have a first end attached to the plunger 18, and a user may depress the plunger rod 19 by applying force to a thumb pad 21 on an opposing second end of the plunger rod 19. The plunger 18 is preferably made from an elastomeric material and has an outer diameter that is slightly larger than the inner diameter of the barrel 20 to provide a seal that prevents leaking of the liquid medicine 11 from the distal end portion 14 into the proximal end portion 12.

The proximal end portion 12 of a syringe, such as a pre-filled syringe is generally open to the atmosphere; however, as illustrated in FIG. 1, the device according to the first embodiment may include a stationary barrier 22, so that the proximal end portion 12 is at least partially sealed from the ambient atmosphere. The stationary barrier 22 may include a central opening through which the plunger rod 19 slides while providing a sealing surface around the outer circumferential surface of the plunger rod 19 and the inner circumferential surface of the barrel 20 of the syringe 10. The stationary barrier 22 may be made from a variety of materials and provided in the form of a solid wall, a resilient washer, baffle(s), or screen, and preferably sufficiently seals the internal volume within the proximal end portion 12 of the barrel 20 from the external ambient atmosphere.

The device further comprises a sensor 24 having two open ends or ports through which air from the exterior atmosphere may be drawn through the sensor 24. In order to detect the flow of ambient air entering the syringe while dispensing drug, the sensor 24 should have one port in fluid communication with the proximal end portion 12 of the syringe barrel 20, and the other port open to atmosphere, the two ports are preferably separated by a barrier to flow sufficient to create a pressure drop across the sensor, such as barrier 22. For example in one configuration, the sensor 24 may be attached to the wall of the syringe 10 adjacent to the barrier 22, such that one of the ports of the sensor 24 is attached to a point between the plunger 18 and the barrier 22 and in fluid communication with the internal volume within the proximal end portion 12 of the syringe 10, while the other port of the sensor 24 is in fluid communication with the external atmosphere. Ambient air may then flow through the sensor 24 (as indicated with arrow B) and into the proximal end portion 12 of the syringe 10 and generate a detectable pressure drop when the plunger 18 is advanced. The sensor 24 is preferably associated with an antenna and a sufficient power source, so that data collected by the sensor 24 may be wirelessly transmitted.

The pressure drop across the sensor should be large enough to be detectable, yet not so large as to impede syringe operation or usability. The device according to the various embodiments disclosed herein should be configured, such that the pressure drop causes a finite flow of air to pass through the sensor. The overall volume of air drawn into the proximal end portion of the syringe may be determined by transmitting the pressure readings from the sensor to a controller having the capability to store data and calculate the flow rate over time to produce a flow curve from which the total volume drawn into the proximal end portion of the syringe may be integrated. This total volume should be approximately equal or at least directly proportional to the volume of liquid medicine leaving the syringe through the orifice in the syringe hub because the syringe is a generally rigid container having a geometry that is substantially identical on both sides of the plunger. The swept volume on both sides of the plunger is essentially equal, except that the plunger rod occupies a finite volume within the proximal end portion of the internal volume of the syringe barrel. However, the dimensions of the portion of the plunger rod occupying the internal volume may be easily calculated or estimated by the controller, for example.

As previously noted, the embodiments disclosed herein takes advantage of a small but finite flow of air entering the open end of a syringe barrel as the plunger moves within it. The devices disclosed herein preferably incorporate a sensor close to the syringe and include a barrier to fluid flow within the syringe barrel that allows the plunger to advance. As one example, a flat washer used as the barrier may be used to provide an adequate pressure drop across the sensor. Alternatively, in a less preferred embodiment, the pressure drop could be implemented as a wall or series of baffles molded into the flow path, such that the path of least resistance of ambient air flow into the proximal end portion of the syringe is through the sensor. In such an embodiment, the volume occupied by the walls or baffles would be accounted for in the calculation by the controller, for example. In yet another embodiment described in greater detail below, the entire syringe may be enclosed in a housing having a fluid path connecting the proximal end portion of the syringe with the atmosphere and a senor located within the fluid path, and the housing may be configured to serve as a barrier. Such a configuration could be used in an autoinjector, for example, to monitor syringe operation without requiring any special adaptation for the syringe.

The devices according the embodiments disclosed herein may be implemented with a mechanical coupling to the syringe, but it is not a requirement. Also, while the ambient fluid drawn into the syringe barrel is likely to be air, the embodiments disclosed herein are also applicable to devices that may utilize a pool of liquid to pressurize the proximal end of the syringe barrel to advance the plunger. Furthermore, there is no limitation to the range of volumes that the devices may detect; therefore, the devices may comprise a syringe of various sizes. Finally, the finite volume of ambient air entering the syringe is of sufficient volume that the sensors should successfully and accurately be able to support the intended use, i.e. monitor and record patient adherence to a therapeutic regiment.

In addition to the above listed aspects, the devices as disclosed herein may detect other information about the syringe or its operation, particularly for autoinjectors or similar devices that utilize a motor to apply a consistent and constant force to advance the plunger. Such additional information may be used to provide warnings or alerts to the patient or healthcare provider. For example, it may be possible to detect the presence of bubbles and/or particulate matter within the drug based wholly on flow anomalies observed during use. Bubbles have the tendency to momentarily increase flow rates as they transit the needle, while particulates decrease flow rates.

The high impedance presented by a small needle orifice to viscous drugs naturally limits the plunger speed for an autoinjector to a range dependent on the viscosity. Therefore, in another example, it may be possible to monitor changes in drug viscosity by detecting plunger speeds outside of an expected range. For example, colder temperatures tend to increase drug viscosity. Because it is not uncommon for certain drugs to be refrigerated before use, patients who use such drugs before allowing them to reach room temperature could experience slower plunger speeds that may be outside the desired range. Needle orifice size also affects plunger speed. As such, any change in needle geometry, which might occur if the needle is bent or occluded, may also result in the detection of a plunger speed outside the expected range.

As previously noted, the devices according to the embodiments disclosed herein are able to calculate the volume of expelled fluid for a range of syringe diameters and the resolution of the measured volume does not decrease as the syringe volume increases. If one were to attempt to calculate the volume of liquid medicine expelled from a syringe by sensing or detecting the axial displacement of the plunger, the volume calculated is dependent on the diameter of the syringe. For example, a typical 1 mL syringe displaces roughly 1 mL of liquid per 35 mm of plunger travel, or 28.5 µL/mm. A typical 3 mL syringe displaces roughly 2.5 mL per 40 mm of plunger travel, or 62.5 µL/mm. Therefore, the difficulty or inaccuracy associated with detecting small incremental changes in axial displacement of the plunger will result in more uncertainty, i.e. lower resolution, of the calculated expelled volume as the diameter of the syringe increases. Because the devices according to the embodiments disclosed herein calculate expelled volume without relying on the detection of plunger displacement, but rather ambient air intake, the resolution in the calculated expelled volumes is maintained as the diameter of the syringe increases.

In yet another aspect, a plunger with a defective seal resulting in liquid medicine leaking into the proximal end portion of the syringe barrel may also be detectible using devices as disclosed herein because the leaked liquid would occupy volume that should otherwise be filled by ambient air. Relying on axial plunger displacement to determine the volume of delivered medicine would not detect such leaks, thereby creating a potentially adverse situation for the patient. When relying on plunger displacement to determine expelled volume, it would be assumed that the patient delivered all of the medicine when the plunger is advanced to the end of the syringe barrel even if a leak were to occur.

Figure 2:
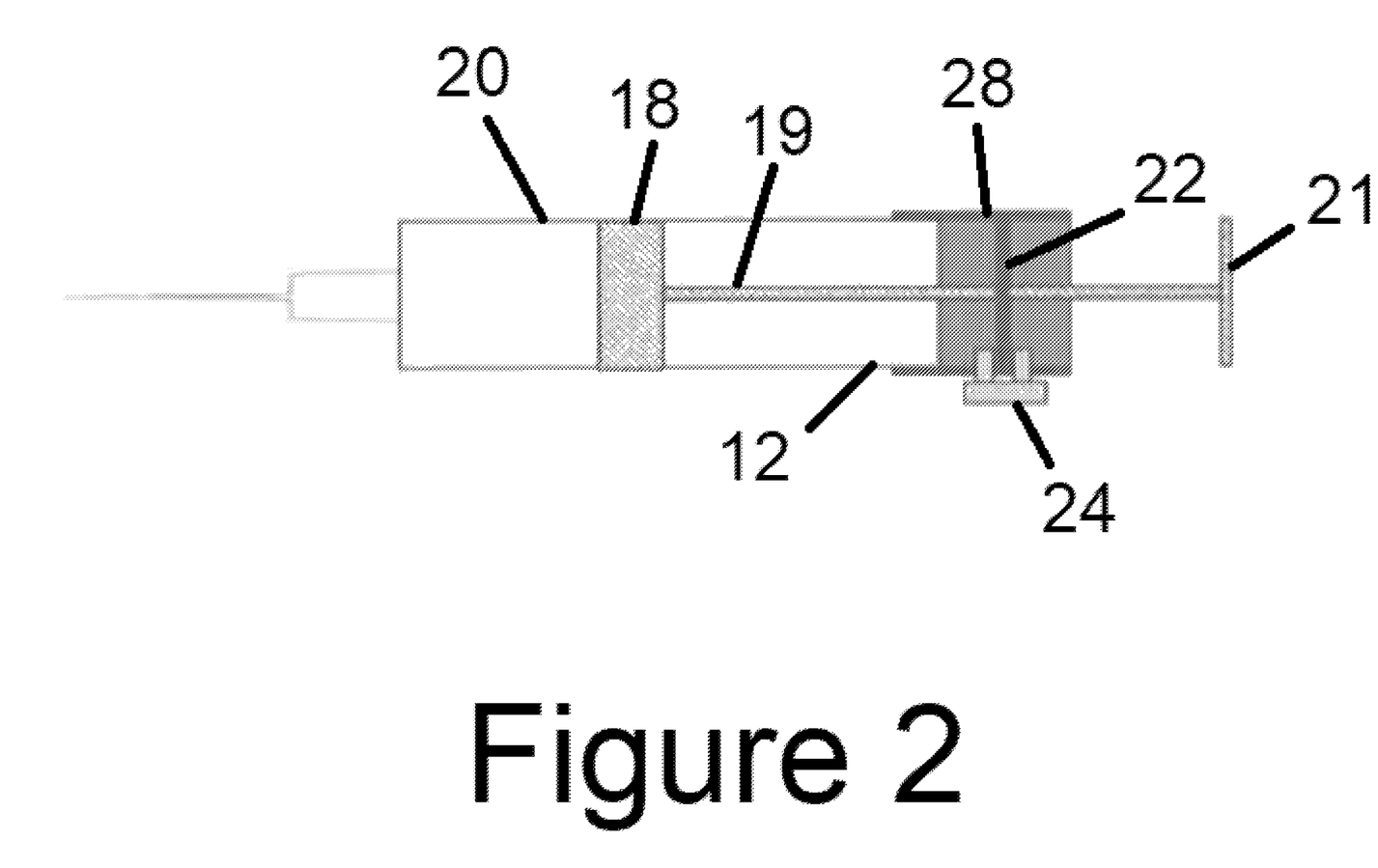
FIG. 2 is a schematic side view of a device according to a second embodiment.

Syringes that are pre-filled are unlikely to be reusable. In the previously described embodiment the barrier is incorporated into the syringe barrel; therefore, after administration of the liquid medicine, the user will likely dispose of the entire device. However, devices according to various embodiments disclosed herein may be configured to be reusable. For example, referring to FIGS. 2 and 3A to 3E, a device according to a second embodiment is provided. Similar to the previously described device, the device of FIG. 2 includes a syringe barrel 20 and a plunger 18 configured to slide within the syringe barrel 20. A plunger rod 19 attached to the plunger 18 enables displacement of the plunger 18. The opposing end of the plunger rod 19 includes a thumb pad 21, so that the plunger rod 19 and plunger 18 may be easily advanced. Unlike the previously described embodiment, the barrier is not installed into the proximal end portion 12 of the syringe barrel 20. Instead a separate reusable extension housing 28 may be attached to the syringe barrel 20 adjacent to the proximal end portion 12. The extension housing 28 is provided with an internal barrier 22, similar to the previously described barrier, such that the barrier 22 is generally perpendicular to the longitudinal axis of the syringe barrel 20 and has a centrally located aperture 23 through which the plunger rod 19 may extend. The sensor 24 may be attached to the wall of the extension housing 28, such that a single port of the sensor 24 is in fluid communication with the internal volume of the housing 28 on one side of the barrier 22, while the other port is in fluid communication with the internal volume on the opposing side of the barrier 22. Upon advancing the plunger 18, ambient air is drawn into the proximal end portion 12 through the sensor 24.

Figure 3A:
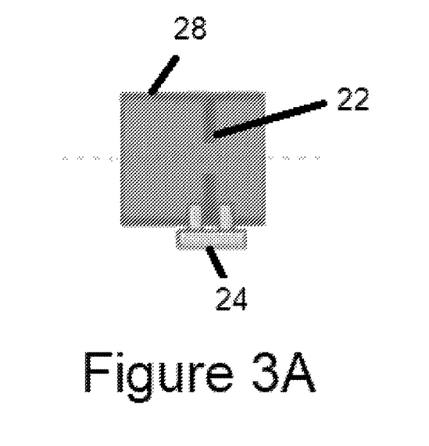
FIG. 3A is a side cross-sectional view of an extension housing included in the second embodiment of FIG. 2.
Figure 3B:
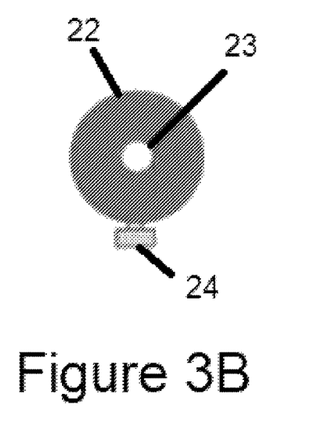
FIG. 3B is a front plan view of the extension housing of FIG. 3A in a closed condition.
Figure 3C:
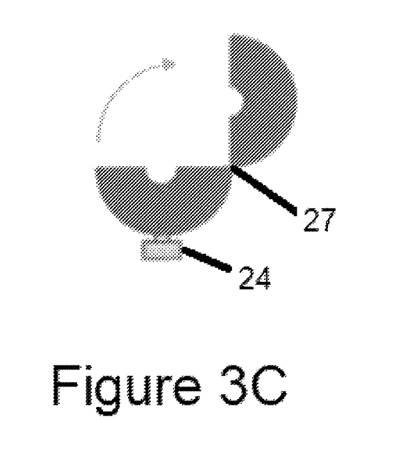
FIG. 3C is a rear view of the extension housing of FIG. 3A in an open condition.
Figure 3D:
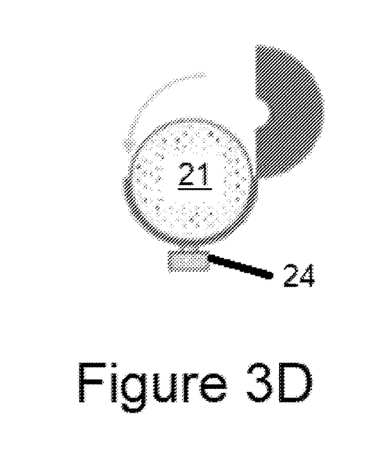
FIG. 3D is a rear view of the extension housing of FIG. 3A in an open condition in combination with a syringe.
Figure 3E:
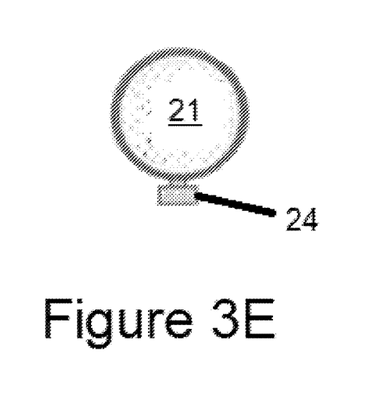
FIG. 3E is a rear view of the extension housing of FIG. 3A in the closed condition in combination with a syringe.

Referring to FIGS. 3A to 3E, the extension housing 28 may, for example, comprise two pieces attached to each other with a hinge 27, so that the housing 28 may be opened and closed similar to a clam-shell configuration. Preferably, the opposing side of the housing 28 relative to the hinge 27 includes a locking feature, such as a clasp (not shown), to maintain the housing 28 in a closed condition during use. In order to install the extension housing 28, the extension housing 28 is opened (FIG. 3C), the user ensures that the plunger rod 19 is located within the aperture 23 and that the open end in the proximal end portion 12 of the syringe barrel 20 is located inside the housing 28 on one side of the barrier 22 (FIG. 3D), and then the extension housing is finally closed (FIG. 3E). It is preferred that the inner diameter of the extension housing 28 is approximately equal to the outer diameter of the syringe barrel 20 to ensure a close, interference fit between the two components. Alternatively, an elastomeric seal, such as an o-ring, may be inserted between the external surface of the syringe barrel 20 and the internal surface of the extension housing 28. In some embodiments, the outer surface of the extension housing 28 may optionally be provided with a finger flange (not shown) to facilitate actuation of the plunger rod 19. After the liquid medicine in the syringe barrel 20 is administered, the extension housing 28 may be opened to remove and dispose of the used syringe. The extension housing 28 may then be attached to a new syringe before the next scheduled dosage. Because the embodiment is reusable, the extension housing 28 may further comprise a power storage means, such as a rechargeable battery (not shown), that can provide sufficient energy for collection and transmission of information detected by the sensor 24.

In an alternative embodiment, the extension housing may be provided as a single piece that does not include a hinge. In order to attach and remove the extension housing, the plunger rod may be detached from the plunger, for example, by unthreading the end of the plunger rod from the plunger. In such a configuration, both the plunger rod and the extension housing would be reusable. A new pre-filled syringe containing medicine may include a plunger without a plunger rod, so that the reusable plunger rod may be threaded into the new plunger and the extension housing attached to the proximal end portion of the new syringe barrel.

Figure 4:
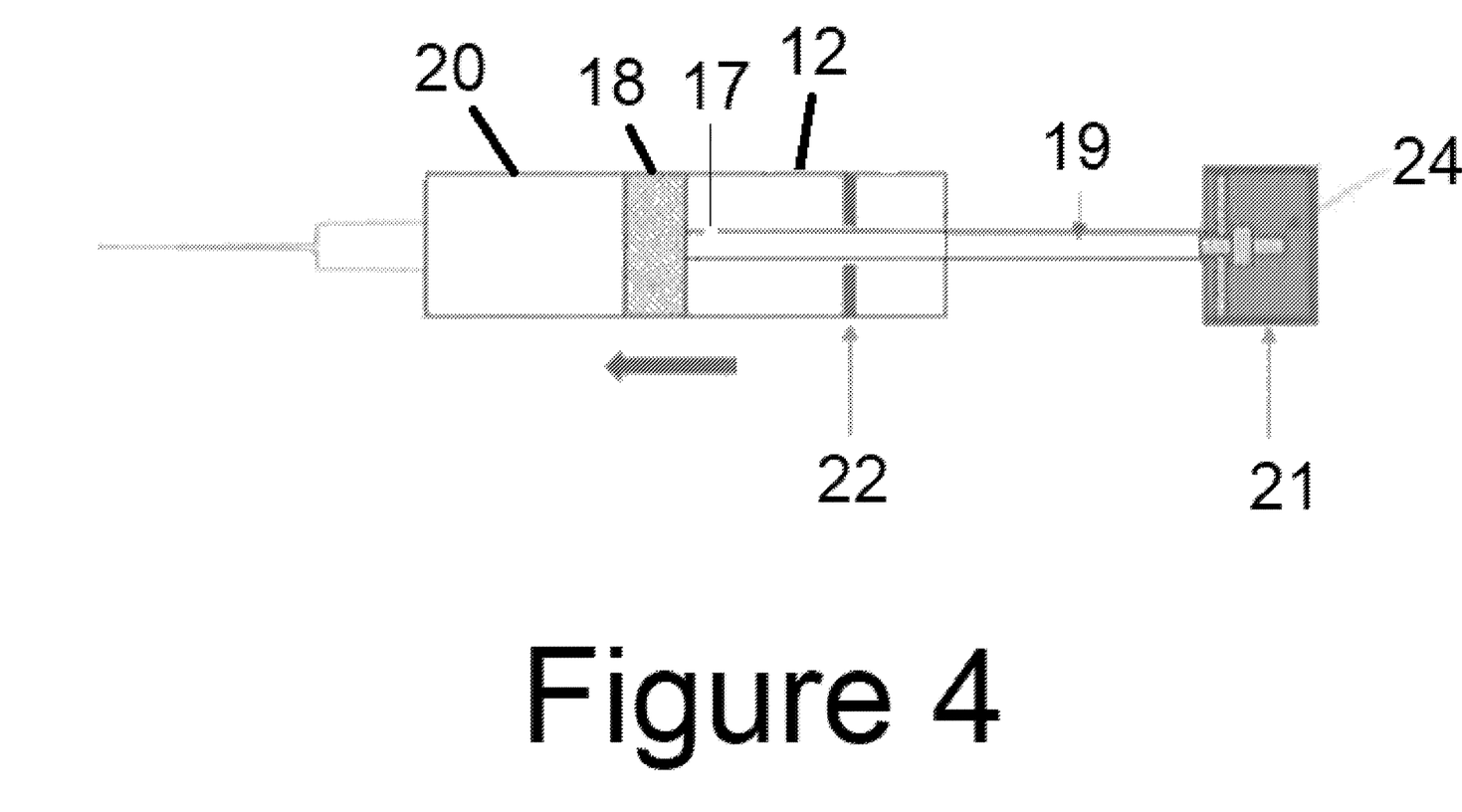
FIG. 4 is a schematic side view of a device according to a third embodiment.

In yet another embodiment, the sensors for determining the volume of expelled fluid may be incorporated entirely within the plunger rod. For example, referring to FIG. 4, a device is provided that is similar to the previously described embodiments in that it includes a syringe barrel 20 and a plunger 18 configured to slide within the syringe barrel 20. A plunger rod 19 attached to the plunger 18 enables displacement of the plunger 18. The opposing end of the plunger rod 19 includes a thumb pad 21, so that the plunger rod 19 and plunger 18 may be easily advanced. A stationary barrier 22 similar to the previously described barriers is located within the proximal end portion 12 of the syringe barrel 20 and includes a central aperture through which the plunger rod 19 extends. Unlike the previously described embodiments, the plunger rod 19 is intentionally hollow and includes an opening 17 proximate the end attached to the plunger 18 and in fluid communication with the internal volume of the proximal end portion 12 of the syringe barrel 20. The opposite end of the plunger rod 19 is attached to one of the ports of a sensor 24, such as a diaphragm sensor, housed within the thumb pad 21, such that the sensor 24 is in fluid communication with the hollow plunger rod 19. A second port of the sensor 24 is open to the ambient atmosphere. The barrier 22 is configured such that the path of least resistance for ambient air entering the proximal end portion 12 of the syringe barrel 20 when the plunger 18 is advanced is through the flow sensor 24, the plunger rod 19, and finally out of the opening 17, thereby creating a pressure drop across the flow sensor 24 that may be detected. This configuration enables most of the electrical components (e.g. sensor, antenna, power storage, etc.) to be housed within the thumb pad 21. For some applications, it may be acceptable to re-use the plunger rod by detaching the plunger rod from the plunger after the liquid medicine is administered, disposing of the empty syringe, and re-attaching the plunger rod to the plunger of a new syringe.

Figure 5:
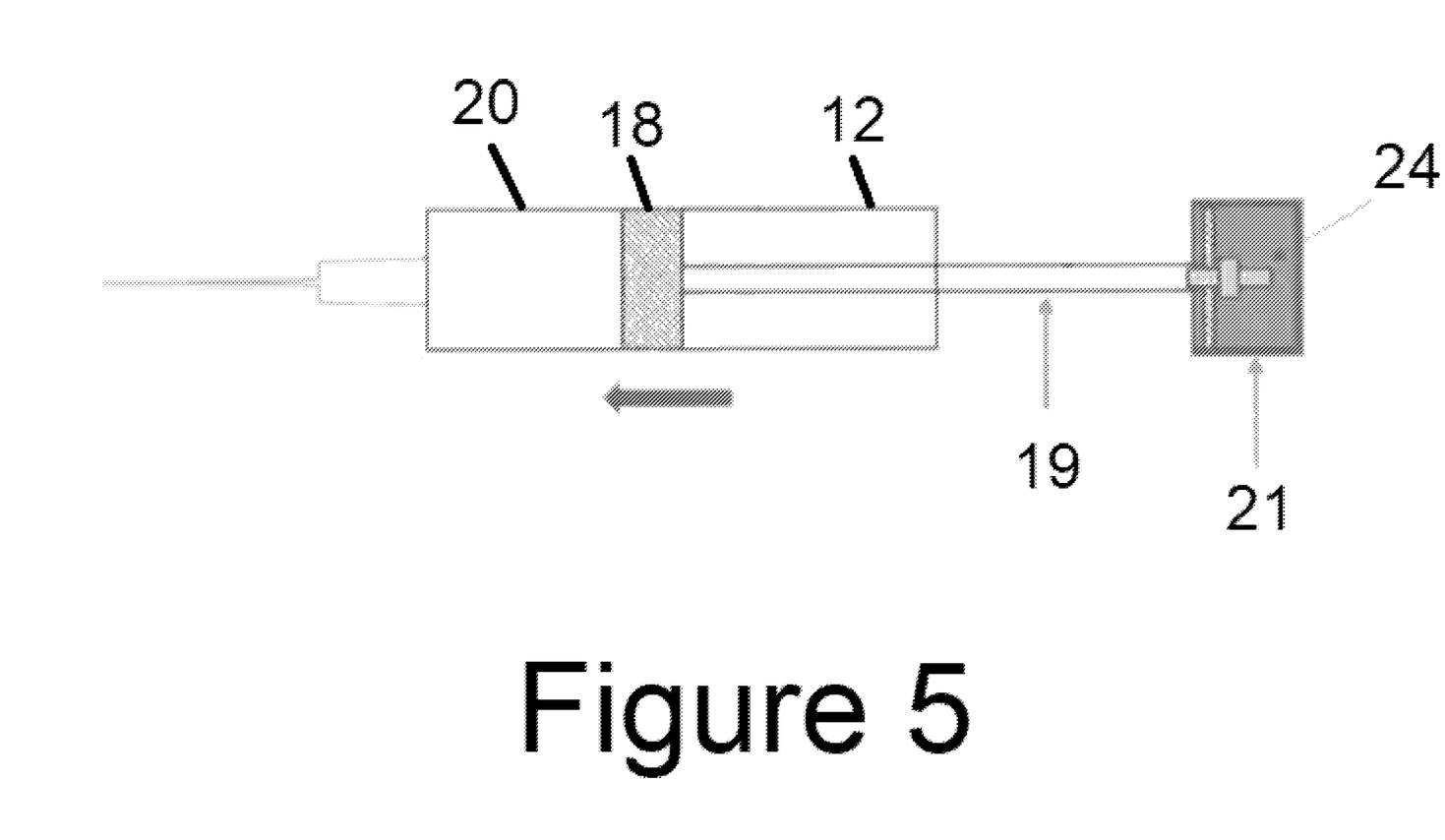
FIG. 5 is a schematic side view of a device according to a fourth embodiment.

In some embodiments, it is not necessary to incorporate an opening in the plunger rod proximate to the plunger. For example, the embodiment of illustrated in FIG. 5 includes a hollow plunger rod 19, similar to the previously described embodiment. However, one end of the hollow plunger rod 19 is closed by the elastomeric plunger 19. A sensor 24 includes a port attached to one end of the hollow plunger rod, while the other port is open to atmosphere. However, air cannot flow through the sensor 24, when the plunger 18 is advanced. Instead, advancing the plunger 18 causes the plunger 18 to deflect, compressing air within the sealed volume within the plunger rod 19. A change in differential pressure is therefore detected by the sensor 24 by comparing the pressure within the hollow plunger rod 19 with the ambient atmospheric pressure, which is a reference pressure. In order to limit sensitivity of the sensor 24 to fluctuations in ambient atmospheric pressure, a small pinhole may be provided in the plunger rod 19 that allows it to slowly equilibrate to local atmospheric pressure.

Various pressure sensors provide for different pressure operating ranges and may be appropriately selected for the syringe used in the devices according to the embodiments described herein. For example, the range of a diaphragm type differential pressure sensor may be ±500 Pa, while a barometric pressure sensor, such as those manufactured by NXP Semiconductors N.V. of Eindhoven, Netherlands or Bosch Sensortec GmbH of Reutlingen, Germany, may operate over a range of tens of thousands of Pascal. Barometric pressure sensors may also be preferable because they operate at low power levels requiring smaller battery size and capacity.

Figure 6:
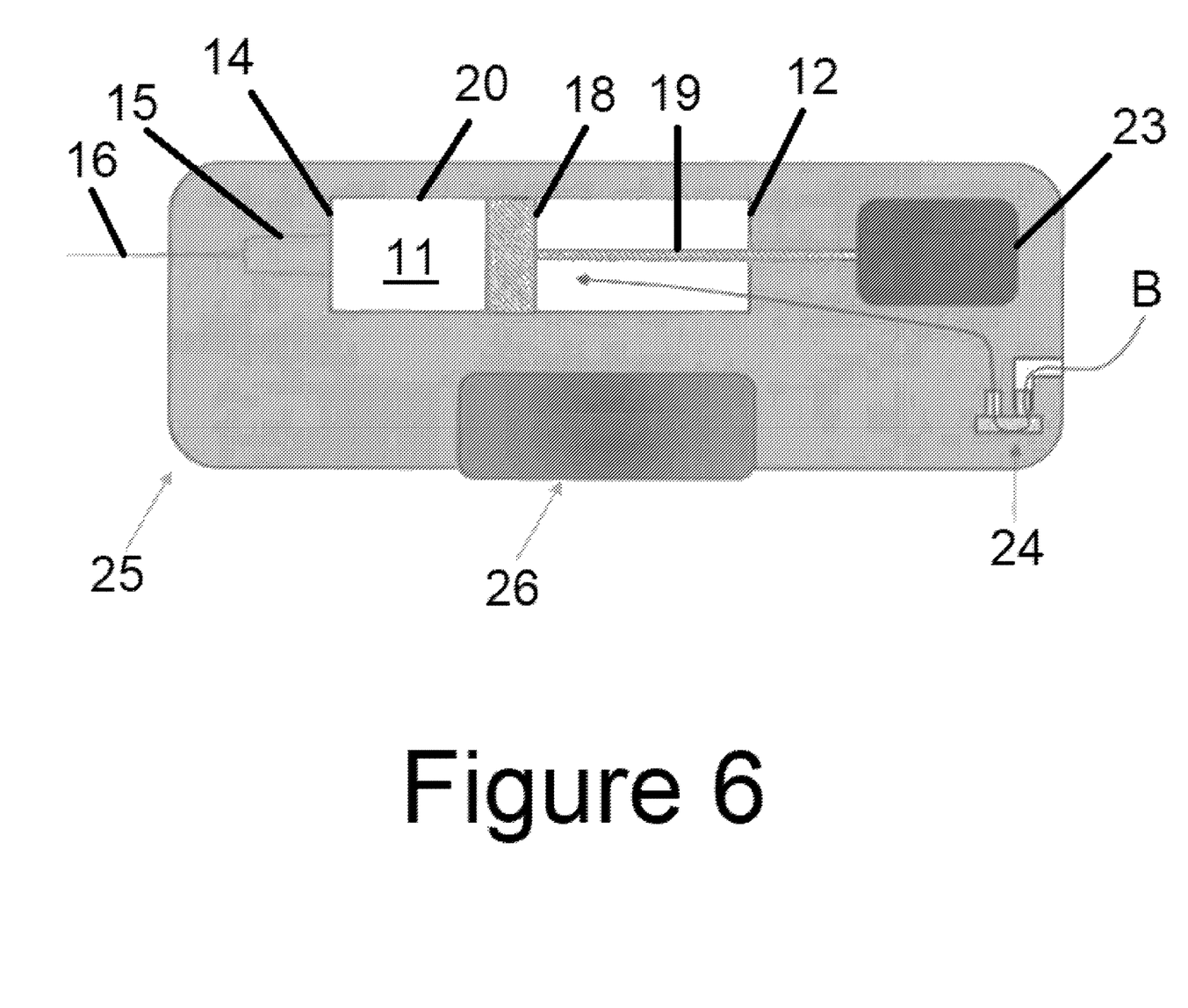
FIG. 6 is a schematic side view of a device according to a fifth embodiment.

As previously mentioned, if a feature of the device can provide a suitable barrier to ambient flow into the proximal end portion of the syringe barrel that results in a pressure drop across the sensor, the inclusion of a specific barrier within the syringe barrel is not necessary. Referring now to FIG. 6, a device according to another embodiment is illustrated that may be provided in the form of an autoinjector, pen injector, or wearable injection device, for example. The device is similar to the previously described embodiments in that the device comprises a syringe barrel 20 having a proximal end portion 12 located on the opposing end of the syringe 10 relative to a distal end portion 14. The distal end portion 14 may also include a hub 15 having an orifice with an optional needle 16 through which liquid medicine 11 contained in the distal end portion 14 may be expelled. In some embodiments, the syringe may comprise with a double ended cannula that is mounted within the housing and a replaceable cartridge, for example.

Again, the syringe barrel 20 has an internal volume that is separated by an elastomeric plunger 18 actuated with a plunger rod 19; however, unlike the previous embodiments, the proximal end of the plunger rod 19 may be mechanically attached to a motor 23, for example, for advancing the plunger 18.

The device of FIG. 6 also differs in that the proximal end portion 12 does not include a stationary barrier. Instead, the device includes a housing 25 having a housing door 26. The housing door 26 provides access to the interior of the housing 25, such that a user may insert a new pre-filled syringe or cartridge filled with medicine. Embedded or installed within the housing is a sensor 24, as previously described. The sensor 24 includes two ports through which air from the exterior atmosphere may flow through the sensor 24 (as indicated with arrow B). Therefore, the sensor 24 should have one port in fluid communication with the proximal end portion 12 of the syringe barrel 20, and the other port open to atmosphere external to the housing 25. The sensor 24 may otherwise be located anywhere within the housing 25. The housing 25 and housing door 26 are preferably configured, such that upon closing the housing door 26, the path of least resistance for ambient air to enter the proximal end portion 12 upon advancing the plunger 18 is through the sensor 24, thereby creating a detectable pressure drop across the sensor. Similar to the previously described re-usable embodiments, it is preferred that the device includes some power storage means sufficient to allow the sensor 24 to collect and transmit data.

Example

Aspects of the embodiments disclosed herein will be further appreciated upon consideration of the following Example, which is intended to illustrate a certain particular embodiment, but is not intended to limit its scope.

Figure 7:
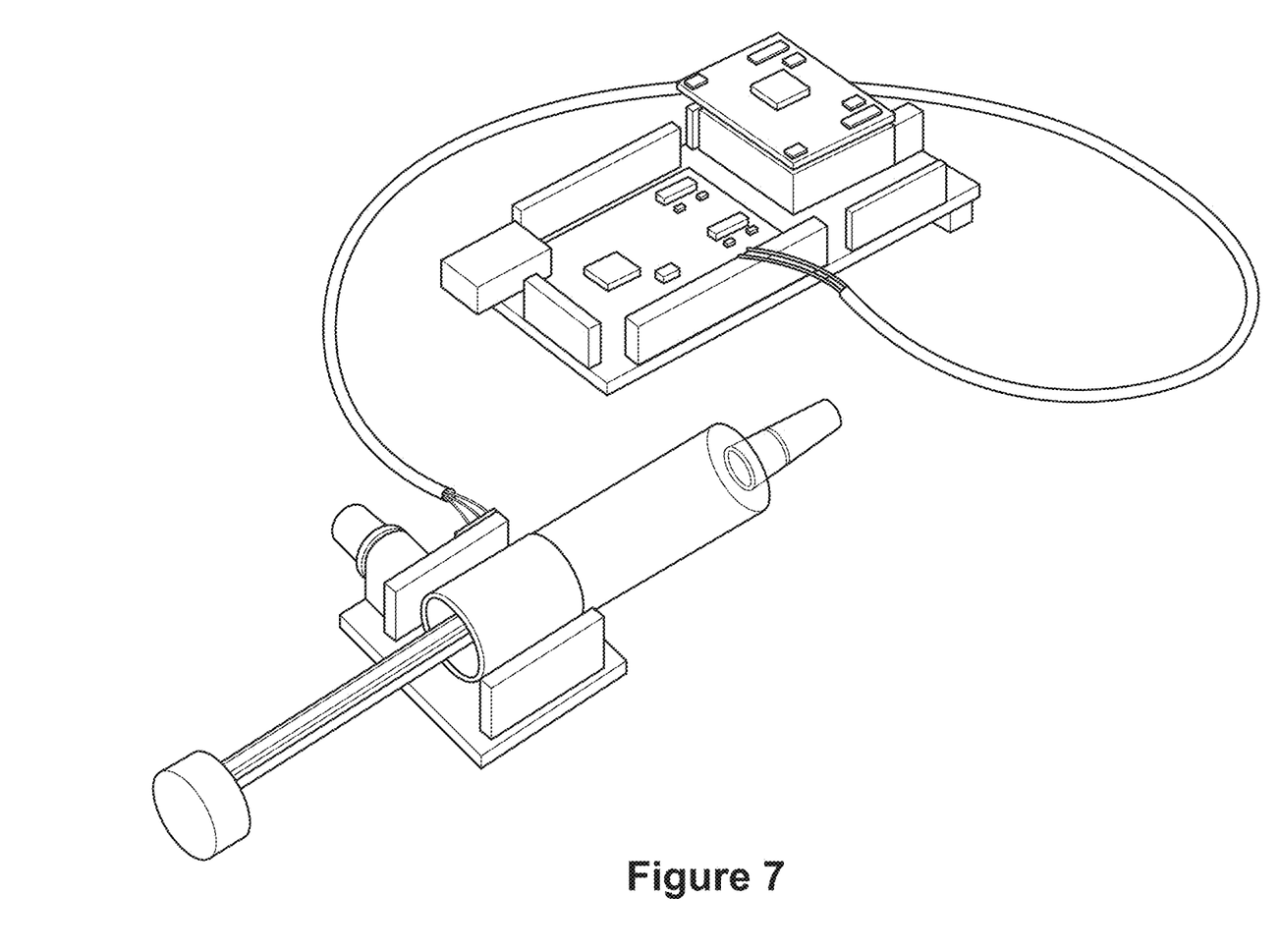
FIG. 7 is a photograph of a 1 mL syringe and sensor combined to provide a device as disclosed herein.

A system similar to the set-up as demonstrated in the photograph of FIG. 7 was prepared using a 1 mL syringe filled with tap water. The open end of the 1 mL syringe was fitted with a housing to serve as a barrier. The syringe and the associated housing were mounted onto a board and connected to a differential pressure, such that one port of the sensor interfaced with the open end of the syringe through the housing and a second port of the sensor was open to atmosphere. The sensor was connected to a microcontroller located on a separate board, which enabled operation and recording of the sensor readings using either custom firmware associated with the microcontroller or a PC. A single depression of the plunger expelled the 1 mL of water in the syringe, and the pressure drop measured by the sensor over time was recorded using a universal asynchronous receiver-transmitter (DART), which allowed the sensor data to be collected on a PC.

Figure 8:
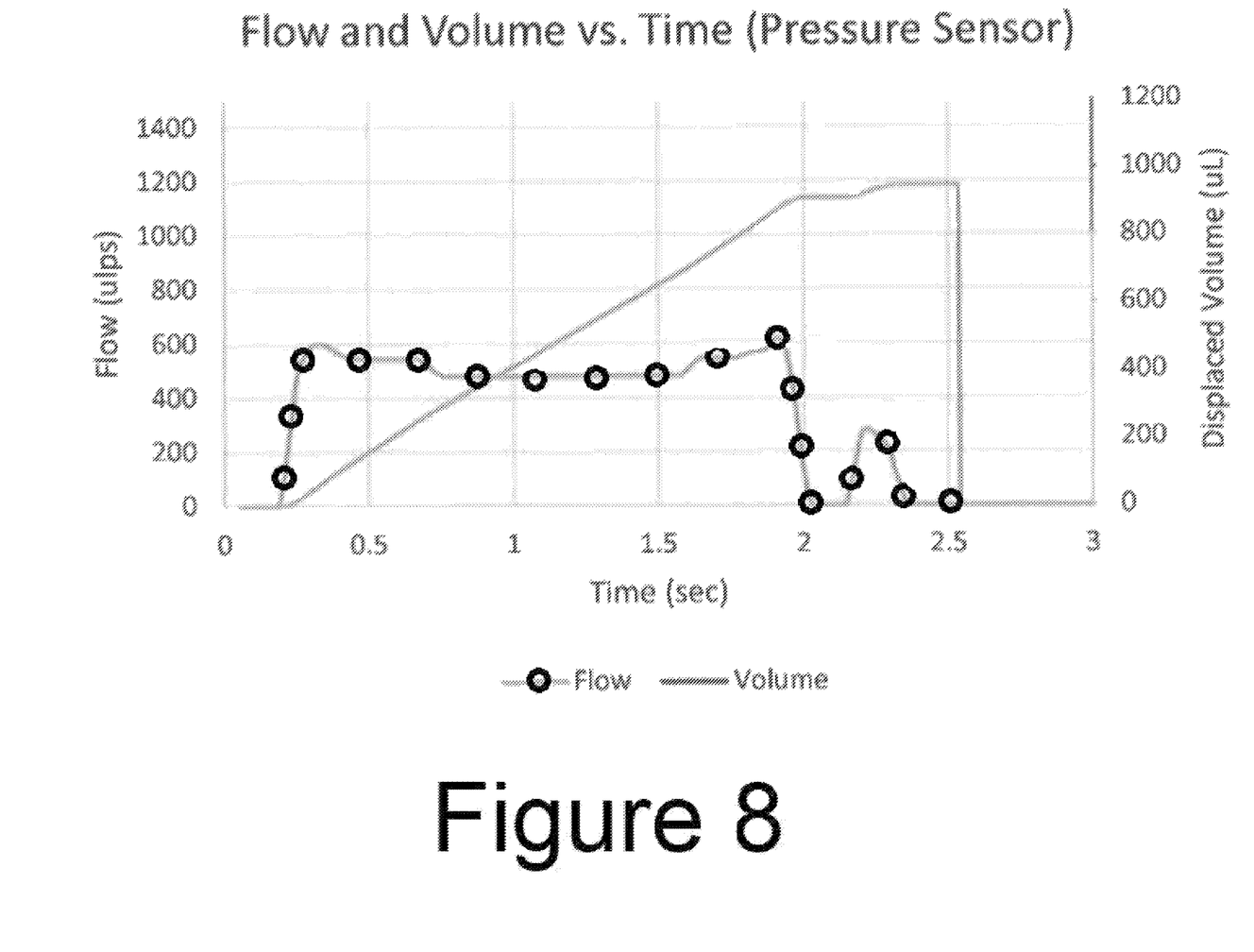
FIG. 8 is a plot of the flow rate and total expelled volume over time calculated using a system similar to the apparatus of FIG. 7.

The flow rate over time calculated from the pressure drop measured by the sensor is presented in the plot of FIG. 8. Integrating the plot of flow rate over time provided the corresponding total volume expelled over time also plotted in FIG. 8. The results demonstrate that the sensor was able to accurately monitor and record the expulsion of 1 mL of liquid from the syringe.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A device comprising:
   a syringe barrel having a proximal end portion and a distal end portion;
   a plunger within the syringe barrel and configured to slide within the syringe barrel from the proximal end portion towards the distal end portion and provide a seal between the proximal end portion and the distal end portion; and
   a sensor having a first and second port, the first port being in fluid communication with the proximal end portion and the second port being in fluid communication with a source of fluid external to the syringe barrel,
   wherein the proximal end portion of the syringe barrel defines a barrier, a first internal volume is disposed between the plunger and the barrier, a second internal volume is disposed between the source of fluid external to the syringe barrel and the barrier, and the second internal volume is open to the source of fluid external to the syringe barrel, and
   wherein the sensor is configured to operate with the second port in fluid communication with the source of fluid external to the syringe barrel via the second internal volume.

2. The device of claim 1, wherein the sensor is a pressure differential sensor.

3. The device of claim 1, further comprising a controller connected to the sensor and configured to record pressure differential readings detected by the sensor.

4. The device of claim 3, wherein the distal end portion of the syringe barrel contains a liquid, and the controller is configured to calculate the total volume of liquid expelled from the syringe barrel from the pressure differential readings.

5. The device of claim 1, wherein the source of fluid is ambient air.

6. The device of claim 1, wherein the distal end portion of the syringe barrel is filled with a liquid.

7. The device of claim 6, wherein the liquid contains a therapeutic agent.

8. The device of claim 1, wherein the barrier is stationary, and the first port is in fluid communication at a point between the barrier and the plunger.

9. The device of claim 1, further comprising an extension housing attached to the proximal end portion of the syringe barrel, the extension housing defining the barrier,
   wherein the barrier is stationary, and the first port is in fluid communication at a point between the barrier and the plunger.

10. The device of claim 1, further comprising a hollow plunger rod having a first end attached to the plunger, a second end in fluid communication with the first port, and an opening proximate to the plunger in fluid communication with the proximal end portion.

11. A method of measuring a volume of liquid expelled from the device according to claim 1, wherein the device further comprises a liquid orifice in the distal end portion of the syringe barrel, the second internal volume of the syringe barrel being filled with a liquid, the method comprising:
  sliding the plunger from the proximal end portion towards the distal end portion to expel liquid through the liquid orifice;
  detecting and recording differential pressure with the sensor over time; and
  calculating the volume of liquid expelled through the liquid orifice from the recorded differential pressure over time.

12. A device comprising:
  a syringe barrel defining an internal volume between a proximal end portion and a distal end portion, the proximal end portion defining a barrier that at least partially seals the proximal end portion;
  a plunger within the syringe barrel and configured to slide within the syringe barrel from the proximal end portion towards the distal end portion and to provide a seal between the proximal end portion and the distal end portion;
  a sensor having a first and second port, the second port being in fluid communication with a source of fluid external to the syringe barrel; and
  a hollow plunger rod having a first end closed by the plunger, a second end in fluid communication with the first port, and an opening in fluid communication with the proximal end portion.

13. The device of claim 12, wherein the plunger is elastomeric.

14. The device of claim 12, wherein the sensor is a pressure differential sensor.

15. The device of claim 12, wherein the sensor is a barometric pressure sensor.

16. The device of claim 12, further comprising a controller connected to the sensor and configured to record pressure differential readings detected by the sensor.

17. The device of claim 16, wherein the distal end portion of the syringe barrel contains a liquid, and the controller is configured to calculate the total volume of liquid expelled from the syringe barrel from the pressure differential readings.

18. The device of claim 12, wherein the source of fluid is ambient air.

19. The device of claim 12, wherein the hollow plunger rod further comprises a thumb pad, and the sensor is housed within the thumb pad.

20. A method of measuring a volume of liquid expelled from the device according to claim 12, wherein the device further comprises a liquid orifice in the distal end portion of the syringe barrel, the distal end portion of the internal volume of the syringe barrel being filled with a liquid, the method comprising:
  sliding the plunger from the proximal end portion towards the distal end portion to expel liquid through the liquid orifice;
  detecting and recording differential pressure with the sensor over time; and
  calculating the volume of liquid expelled through the liquid orifice from the recorded differential pressure over time.

* * * * *